United States Patent [19]

Igarashi

[11] Patent Number: 5,948,451
[45] Date of Patent: Sep. 7, 1999

[54] METHOD OF MODIFYING THE BALANCE OF OMEGA UNSATURATED FATTY ACIDS USING A DIOXABICYCLO OCTANE DERIVATIVE

[75] Inventor: Osamu Igarashi, Tokyo, Japan

[73] Assignee: Suntory Limited, Osaka, Japan

[21] Appl. No.: 08/793,316

[22] PCT Filed: Jul. 4, 1996

[86] PCT No.: PCT/JP96/01858
  § 371 Date: Mar. 4, 1997
  § 102(e) Date: Mar. 4, 1997

[87] PCT Pub. No.: WO97/01968
  PCT Pub. Date: Jan. 23, 1997

[30] Foreign Application Priority Data

Jul. 4, 1995 [JP] Japan ................................. 7-168742

[51] Int. Cl.⁶ ......................................................... A23D 9/00
[52] U.S. Cl. ............................ 426/2; 426/601; 426/541; 424/439
[58] Field of Search ............................. 426/601, 2, 541; 424/439

[56] References Cited

FOREIGN PATENT DOCUMENTS

| | | |
|---|---|---|
| 0 387 000 | 9/1990 | European Pat. Off. . |
| 0 409 654 | 1/1991 | European Pat. Off. . |
| 0 519 673 | 12/1992 | European Pat. Off. . |
| 3-52866 | 3/1991 | Japan . |
| 3-280855 | 12/1991 | Japan . |
| 3-368326 | 12/1992 | Japan . |

*Primary Examiner*—Carolyn Paden
*Attorney, Agent, or Firm*—Burns, Doane, Swecker & Mathis, L.L.P.

[57] ABSTRACT

The present invention discloses an omega-3/omega-6 unsaturated fatty acid balance modifying composition whose active ingredient is a dioxabicyclo(3.3.0)octane derivative represented with general formula (I):

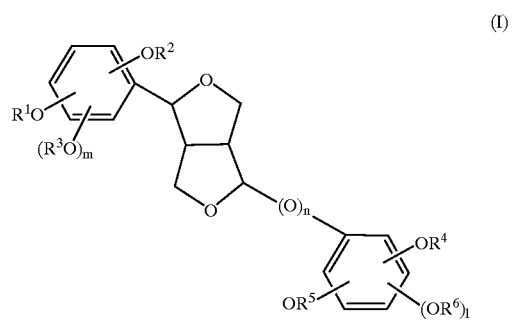

(wherein, $R^1$, $R^2$, $R^3$, $R^4$, $R^5$ and $R^6$ are respectively and independently a hydrogen atom or alkyl group having 1–3 carbon atoms, or $R^1$ and $R^2$ and/or $R^4$ and $R^5$ together represent a methylene group or ethylene group, and n, m and l represent 0 or 1).

6 Claims, 2 Drawing Sheets

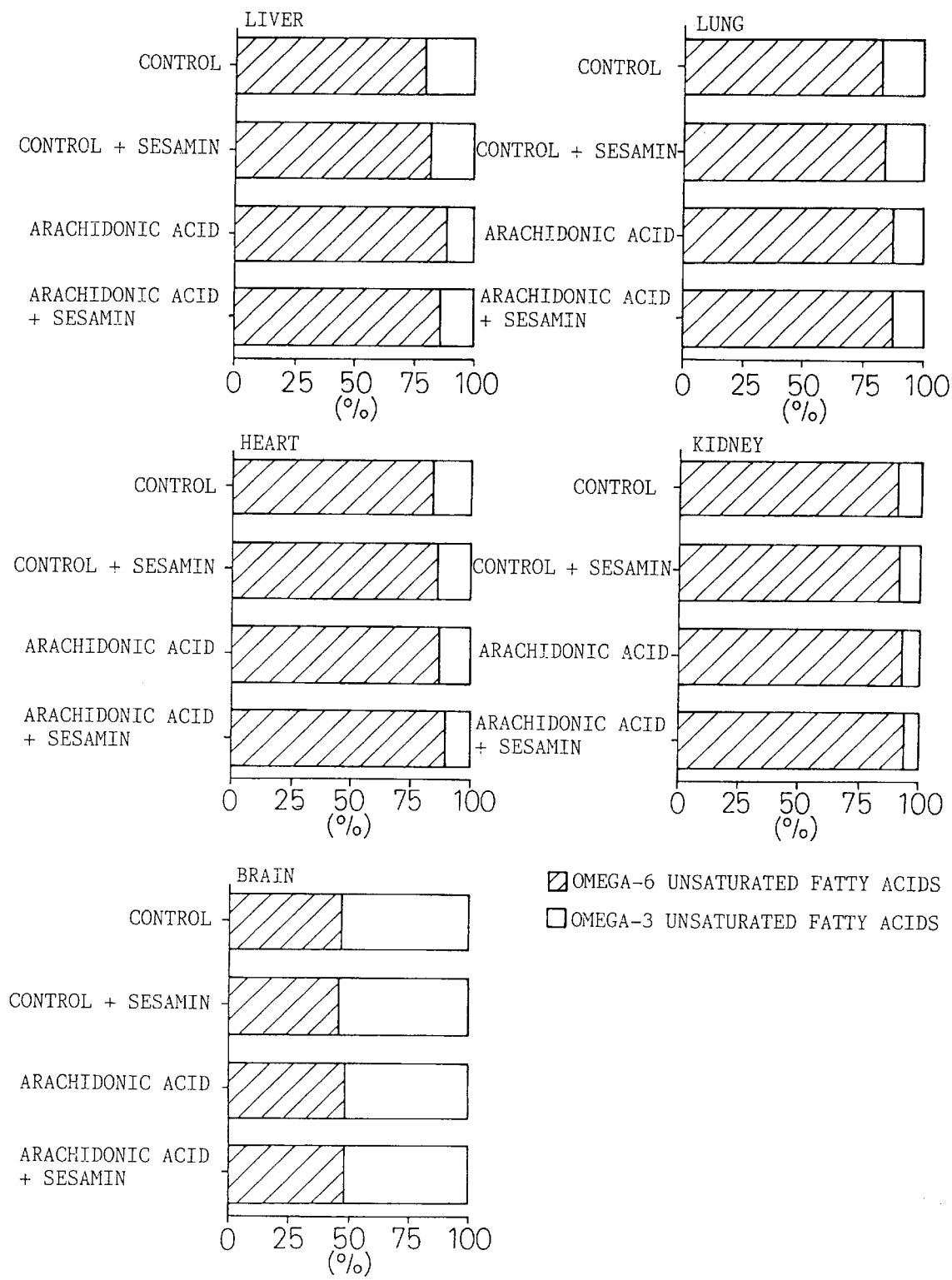

METHOD OF MODIFYING THE BALANCE OF OMEGA UNSATURATED FATTY ACIDS USING A DIOXABICYCLO OCTANE DERIVATIVE

TECHNICAL FIELD

The present invention relates to a food composition containing an omega-6/omega-3 unsaturated fatty acid balance modifier whose active ingredient is a dioxabicyclo (3.3.0)octane derivative, and to an omega-6/omega-3 unsaturated fatty acid balance modifier.

BACKGROUND ART

Since polyunsaturated fatty acids are essential fatty acids, the amount ingested for satisfying the required amount from a nutritional viewpoint has been discussed. At present, however, since the ingested amount is sufficient, attention has focused on serum lipid lowering effects, resulting in a situation in which emphasis is placed on the ratio of unsaturated fatty acids to saturated fatty acids of ingested fats. On the other hand, there are two representatives series of unsaturated fatty acids, namely omega-3 and omega-6 (omega indicates the number of carbon atoms from the terminal methyl group of the fatty acid to the carbon atom at which the first double bond is located). Recently, a growing emphasis has come to be placed on the ratio of these omega-6 fatty acids to omega-3 fatty acids.

Although it has been confirmed that various fatty acids such as omega-6 fatty acids, including linoleic acid, dihomo-γ-linolenic acid and arachidonic acid, and omega-3 fatty acids, including α-linolenic acid, eicosapentaenoic acid and docosahexaenoic acid, exhibit different physiological actions, at the same time, what is important is that these two series of unsaturated fatty acids mutually have a potent effect on the physiological action of the other, as well as that both of these series of fatty acids cannot be biosynthesized in the body, both series are not interchangeable, and the ratio of omega-3 and omega-6 unsaturated fatty acids in the body reflects that in the diet.

In view of these circumstances, Japanese Unexamined Patent Publication No. 3-53869 discloses a food in which the fatty acid composition therein is adjusted so that the ratio of omega-3 fatty acids to omega-6 fatty acids is 1:1 to 1:5. In the revision of Japanese nutritional requirements of 1994 (Japanese Ministry of Health and Welfare, 5th Revision of Japanese Nutritional Requirements, pp. 56–58, 1994), it is stated that the preferable ratio of omega-6 unsaturated fatty acids to omega-3 unsaturated fatty acids is 4:1. However, it is difficult during the daily life to ingest only foods in which the ratio of omega-6 and omega-3 fatty acids is adjusted, and is essentially difficult to constantly keep in mind the ingestion ratio of omega-6 and omega-3 unsaturated fatty acids.

In addition, since the Japanese diet has been Westernized recently, there has been a considerable increase in the opportunities to consume meals made primarily of meat resulting in an increase in the ingestion of omega-6 fatty acids in comparison with omega-3 fatty acids. Due to this trend, there has been a dramatic increase in the mortality rate due to arteriosclerotic diseases such as myocardial infarction and cerebral thrombosis. In order to improve this situation, foods and nutritional supplements have been developed to which have been added omega-3 unsaturated fatty acids such as eicosapentaenoic acid and docosahexaenoic acid concentrated to high concentrations. However, in considering actual dietary habits, it is virtually impossible to consume only one type of fatty acid. In particular, it is dangerous to ingest large amount of only one of these types of unsaturated fatty acids in consideration of the physiological functions of omega-3 and omega-6 unsaturated fatty acids.

For instance, examples of metabolic disorders thought to occur due to ingestion of large amounts of omega-6 unsaturated fatty acids include: (1) disturbance in the balance of eicosanoid production (promotion of thrombus formation, arteriosclerosis and allergic reactions), (2) accelerated gallstone formation, (3) promotion of cancer cell growth (including breast cancer and colon cancer), and (4) depressed immunity and reduced phagocyte function. In addition, examples of metabolic disorders thought to occur accompanying excessive ingestion of omega-3 unsaturated fatty acids (and particularly fish oil containing eicosapentaenoic acid and docosahexaenoic acid) include: (1) myocardial necrosis, (2) liver disorders and decreased liver function, (3) increased sensitivity to catecholamines, and (4) myocardial lipidosis caused by long-chain monoenic acids, increased bleeding time, and greater susceptibility to hemorrhaging and clotting difficulties due to reduced platelet levels.

As has been described above, when referring to unsaturated fatty acids, it is not appropriate to refer to omega-6 series or omega-3 series fatty acids alone. In order to maintain homeostasis of the body and prevent disease, the ingestion ratio of omega-6 and omega-3 series unsaturated fatty acids among the unsaturated fatty acids ingested must be balanced. In addition, those omega-6 unsaturated fatty acids which can be obtained from a normal diet mainly comprise linoleic acid, while the majority of omega-3 unsaturated fatty acids are α-linolenic acid or eicosapentaenoic acid and docosahexaenoic acid from fish oil.

Since it is known that eicosapentaenoic acid and docosahexaenoic acid inhibit conversion from linoleic acid to dihomo-γ-linolenic acid and arachidonic acid (precursors of omega-6 eicosanoids), the balance of these unsaturated fatty acids has an effect on the fatty acid composition of the body, which effect is greater than their actual consumption ratio. Thus, it is extremely difficult to determine the ingestion ratio and its amounts in consideration of dynamics in the body. Therefore, there was a strong desire to develop a safe substance that suitably adjusts the ratio of omega-6 unsaturated fatty acids and omega-3 unsaturated fatty acids in the body in order to maintain homeostasis of the body as well as prevent disease.

DISCLOSURE OF THE INVENTION

Thus, the present invention provides a food composition containing an omega-6/omega-3 unsaturated fatty acid balance modifier whose its active ingredient is a dioxabicyclo (3.3.0)octane derivative, and to an omega-6/omega-3 unsaturated fatty acid balance modifier.

As a result of various research to achieve the above-mentioned object of the present invention, the inventors of the present invention found that dioxabicyclo(3.3.0)octane derivatives obtained by isolation from sesame seeds, sesame oil and by-products of the sesame oil manufacturing process or by synthesis have the effect of modifying the balance of omega-6 and omega-3 unsaturated fatty acids while also having a high degree of safety, thereby leading to completion of the present invention.

Thus, the present invention provides an omega-6/omega-3 unsaturated fatty acid balance modifier, or a food composition containing said modifier, whose active ingredient is the dioxabicyclo(3.3.0)octane derivative, represented with the following general formula (I):

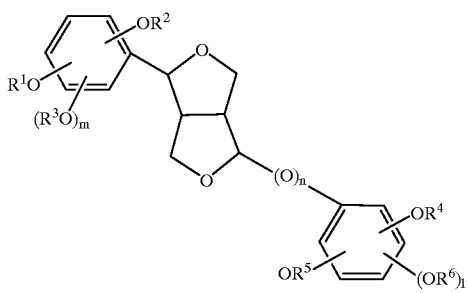

(wherein, $R^1$, $R^2$, $R^3$, $R^4$, $R^5$ and $R^6$ are respectively and independently a hydrogen atom or alkyl group having 1 to 3 carbon atoms, or $R^1$ and $R^2$ and/or $R^4$ and $R^5$ together represent a methylene group or ethylene group, and n, m and l represent 0 or 1).

BRIEF DESCRIPTION OF THE DRAWINGS

FIG. 2 is a graph showing the proportions of omega-3 and omega-6 unsaturated fatty acids in the liver, lung, heart, kidney and brain of male Wistar rats fed with linoleic acid or arachidonic acid with and without a mixture of sesamin and episesamin.

DETAILED EXPLANATION

Figure 1:
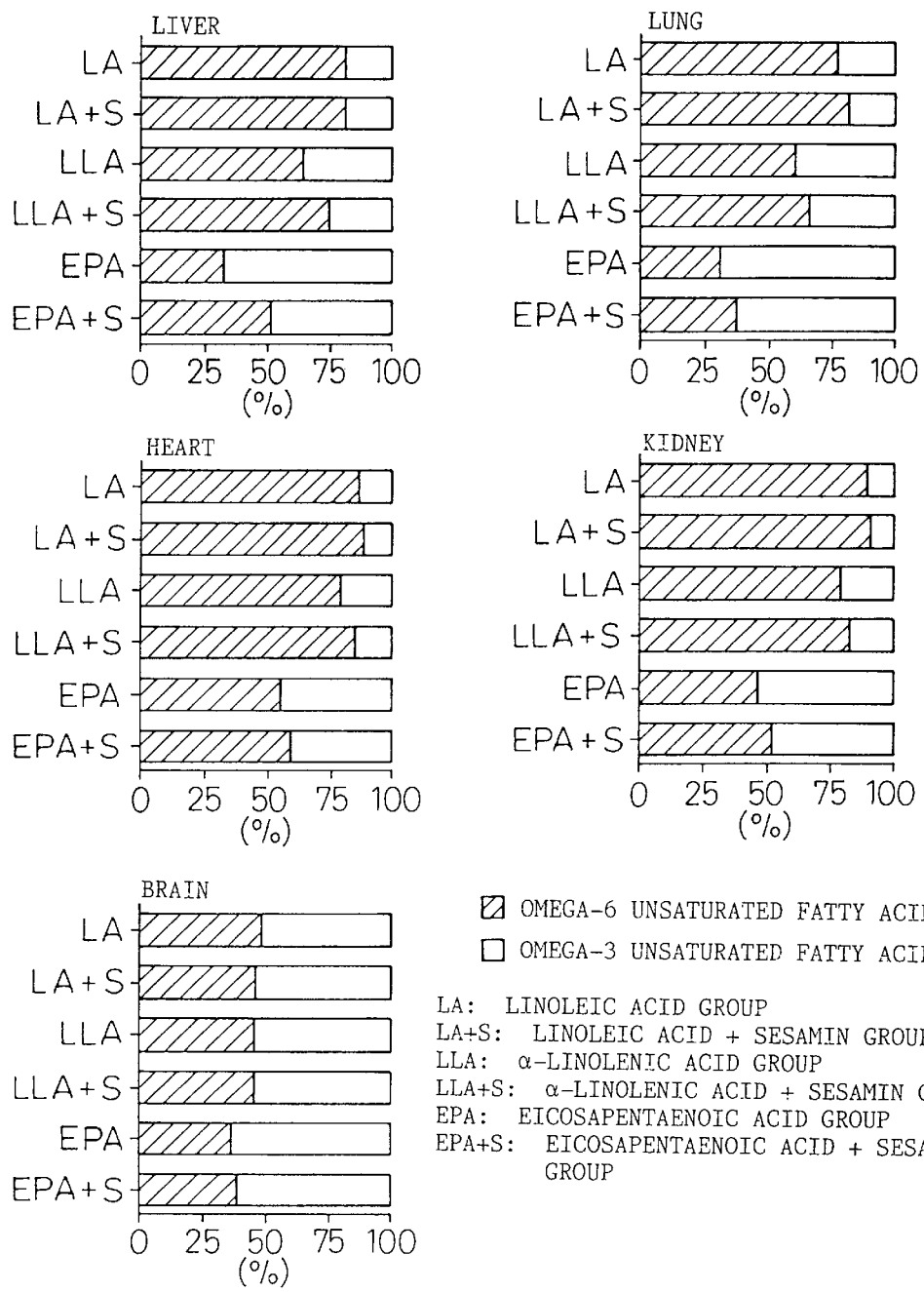
FIG. 1 is a graph showing the proportions of omega-3 unsaturated fatty acid and omega-6 unsaturated fatty acid in the liver, lung, heart, kidney and brain of male Wistar rats fed with linoleic acid, α-linolenic acid or eicosapentaenoic acid with and without a mixture of sesamin and episesamin.

The dioxabicyclo(3.3.0)octane derivatives that are the active ingredients of the present invention are a compound represented with the following general formula (I):

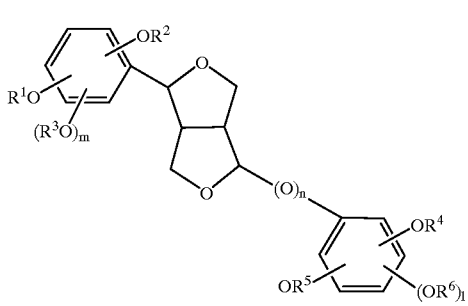

(wherein, $R^1$, $R^2$, $R^3$, $R^4$, $R^5$ and $R^6$ are respectively and independently a hydrogen atom or alkyl group having 1 to 3 carbon atoms, or $R^1$ and $R^2$ and/or $R^4$ and $R^5$ together represent a methylene group or ethylene group, and n, m and l represent 0 or 1). Here, examples of an alkyl group having 1 to 3 carbon atoms include a methyl group, ethyl group, n-propyl group and isopropyl group.

Moreover, specific examples of this compounds include sesamin, sesaminol, episesamin, episesaminol, sesamolin, 2-(3,4-methylenedioxyphenyl)-6-(3-methoxy-4-hydroxyphenyl)-3,7-dioxabicyclo(3.3.0)octane, 2,6-bis-(3-methoxy-4-hydroxyphenyl)-3,7-dioxabicyclo(3.3.0)octane, and 2-(3,4-methylenedioxyphenyl)-6-(3-methoxy-4-hydroxyphenoxy)-3,7-dioxabicyclo(3.3.0)octane. These compounds may be in the form of glycosides, and optically active substances and isomers are also included in the invention of the present application.

In the present invention, the above-mentioned dioxabicyclo(3.3.0)octane derivatives (to be referred to as the derivatives of the present invention) can be used alone or in a combination of two or more. In addition, in the present invention, the derivatives of the present invention are not limited to highly pure purification products, but rather substances can also be used that contain the derivatives of the present invention which are obtained from naturally-occurring substances that contain the derivative of the present invention as well as substances obtained by isolation procedures such as water vapor distillation and molecular distillation (e.g. the methods described in Japanese Examined Patent Publication No. 7-25764 and Japanese Unexamined Patent Publication No. 6-169784). Examples of naturally-occurring substances that contain the derivative of the present invention include sesame oil, by-products of the sesame oil manufacturing process (e.g. defatted dregs of sesame seeds and deodorized scum of sesame oil), sesame seeds, Gokahi, Toboku, Hakka Juhi, Hihutsu, Saishin or cultures obtained by culturing reproductive cells derived from sesame plant (Japanese Unexamined Patent Publication No. 63-207389).

In addition, the compound containing the derivatives of the present invention should contain at least 0.2 wt %, preferably at least 2.0 wt % and more preferably at least 10.0 wt % of the derivatives of the present invention, and more particularly, the total content of sesamin, episesamin, sesaminol, episesaminol and sesamolin should be at least 0.1 wt %, preferably at least 1.0 wt % and more preferably at least 5.0 wt %.

For example, in order to obtain a product containing the derivatives of the present invention by extraction from sesame oil, it can be extracted and concentrated using various organic solvents that are substantially immiscible with sesame oil and are able to extract and dissolve the derivative of the present invention (e.g. acetone, methylethyl ketone, diethyl ketone, methanol and ethanol). One example of a method for obtaining the product containing the derivative of the present invention involves uniformly mixing sesame oil with any of the above-mentioned solvents, allowing the mixture to stand undisturbed at a low temperature, performing phase separation in accordance with routine methods such as centrifugal separation, and distilling off the solvent from the solvent fraction. More specifically, after dissolving sesame oil in 2 to 10 volumes, and preferably 6 to 8 volumes, of acetone, the solution is allowed to stand undisturbed overnight at −80° C., the resulting oil component forms a precipitate, and the acetone is removed from the filtrate obtained by filtration to obtain an extract having as its main ingredient the derivative of the present invention.

In addition, another method for obtaining a product containing the derivative of the present invention comprises mixing sesame oil with hot methanol or hot ethanol, allowing the mixture to stand undisturbed at room temperature and distilling off the solvent from the solvent fraction. More specifically, after vigorously mixing sesame oil with 2 to 10 volumes, and preferably 5 to 7 volumes, of hot methanol (50° C. or higher) or hot ethanol (50° C. or higher), phase separation is carried out in accordance with routine methods such as by standing the mixture undisturbed at room temperature or by centrifugal separation, and the solvent is distilled off from the solvent fraction to obtain an extract having for its main ingredient the derivative of the present invention. Moreover, the extract can also be obtained by utilizing super-critical gas extraction. The sesame oil to be used may be a finished product or any of the crude products in the production process of sesame oil prior to the decoloring step.

In addition, in order to obtain a product containing the derivative of the present invention by extraction from sesame seeds or the defatted products sesame seeds (residual oil content: 8 to 10%), after crushing the sesame seeds or defatted products as necessary, extraction can be performed in accordance with routine methods using any solvent such as the same solvents used in extraction from sesame oil as described above. After separating the extraction residue, the solvent is removed from the extract liquid by evaporation and so forth to obtain the extract.

To obtain the derivative of the present invention, the target compound can be isolated from a product containing the derivative of the present invention separated according to the methods described above, by treating in accordance with routine methods such as column chromatography, high-performance liquid chromatography, recrystallization, distillation and liquid-liquid exchange distribution chromatography.

More specifically, after fractionating the above-mentioned extract with high-performance liquid chromatography using a reverse phase column ($5C_{18}$) and methanol/water (60:40) for the eluent, and distilling off the solvent, the resulting crystals are recrystallized with ethanol to obtain a derivative of the present invention such as sesamin, sesaminol, episesamin, episesaminol, sesamolin, 2-(3,4-methylenedioxyphenyl)-6-(3-methoxy-4-hydroxyphenyl)-3,7-dioxabicyclo(3.3.0)octane, 2,6-bis-(3-methoxy-4-hydroxyphenyl)-3,7-dioxabicyclo(3.3.0)octane, and 2-(3,4-methylenedioxyphenyl)-6-(3-methoxy-4-hydroxyphenoxy)-3,7-dioxabicyclo(3.3.0)octane. Furthermore, the methods for obtaining and purifying the derivative of the present invention and products containing said derivative are not limited to those described above.

In addition, the derivative of the present invention can also be obtained by synthesis in accordance with routine methods.

For example, sesamin and episesamin can be synthesized with the method of Beroza et al. (J. Am. Chem. Soc. 78, 1242 (1956)), pinoresinol ($R^1=R^4=H$, $R^2=R^5=CH_3$ and n=m=l=0 in general formula (I)) can be synthesized with the method of Freundenberg et al. (Chem. Ber., 86, 1157 (1953)), and silingaresinol ($R^1=R^4=H$, $R^2=R^3=R^5=R^6=CH_3$, n=0 and m=l=1 in general formula (I)) can be synthesized with the method of Freundenberg et al. (Chem. Ber., 88, 16 (1955)).

Moreover, the derivative of the present invention can be used in combination with an antioxidant. Examples of antioxidants include natural antioxidants such as tocopherols, flavone derivatives, phyllodulcins, kojic acid, gallic acid derivatives, catechins, fukinolic acid, gossypol, pyrazine derivatives, sesamol, guaiacol, guaiac resin, p-coumalic acid, nordihydroguaiaretic acid, sterols, terpenes, nucleic acid bases and carotenoides, or synthetic antioxidants represented by butylhydroxyanisol (BHA), butylhydroxytoluene (BHT), monotertiary-butylhydroquinone (TBHQ) and 4-hydroxymethyl-2,6-di-tertiary-butylphenol (HMBP).

Among the above-mentioned antioxidants, tocopherols are preferable, examples of which include α-tocopherol, β-tocopherol, γ-tocopherol, δ-tocopherol, ε-tocopherol, ξ-tocopherol, η-tocopherol and tocopherol ester (e.g. tocopherol acetate). Moreover, examples of carotenoids include β-carotene, cantaxanthine and astaxanthine.

Although there are no particular restrictions on the blending ratio of the derivative of the present invention and antioxidant, 0.001 to 1000 parts by weight of antioxidant per 1 part by weight of the derivative of the present invention is desirable. Moreover, a range of 0.01 to 100 parts by weight is preferable, and a range of 0.1 to 100 parts by weight is more preferable.

In the present invention, "omega-6/omega-3 unsaturated fatty acid balance" or simply "balance" refers to the ratio between omega-3 unsaturated fatty acids and omega-6 unsaturated fatty acids in the body. For example, the ratio of omega-3 unsaturated fatty acids and omega-6 unsaturated fatty acids in the liver or serum can be used as an indicator. Here, omega-3 unsaturated fatty acids refer to 9,12,15-octadecatrienoic acid (also referred to as α-linolenic acid "LLA"), 6,9,12,15-octadecatetraenoic acid, 8,11,14,17-eicosatetraenoic acid, 5,8,11,14,17-eicosapentaenoic acid (also referred to as "EPA"), 7,10,13,16,19-docosapentaenoic acid and 4,7,10,13,16,19-docosahexaenoic acid (also referred to as "DHA"), while omega-6 unsaturated fatty acids refer to 9,12-octadecadienoic acid (linoleic acid), 6,9,12,-octadecatrienoic acid (also referred to as γ-linolenic acid, "GLA"), 8,11,14-eicosatrienoic acid (also referred to as dihomo-γ-linolenic acid, "DGLA") and 5,8,11,14-eicosatetraenoic acid (also referred to as arachidonic acid, "AA").

In addition, "balance modification" refers to the action of recovering the balance destroyed by excessive ingestion of omega-3 unsaturated fatty acids or omega-6 unsaturated fatty acids to the normal balance to be inherently maintained in the body. The normal balance to be inherently maintained in the body refers to the balance of omega-3 unsaturated fatty acids and omega-6 unsaturated fatty acids in the body when omega-6 unsaturated fatty acids (n-6) and omega-3 unsaturated fatty acids (n-3) are ingested in a ratio of n-6/n-3=1 to 5 and preferably 2 to 4. For example, the balance in the liver is n-6/n-3=1 to 6 and preferably 2 to 5. However, this balance is not always limited to these values due to the presence of individual differences.

This balance modification is thought to be performed by lowering the level of omega-3 unsaturated fatty acids that has risen above the normal value and raising the level of omega-6 unsaturated fatty acids that fallen below the normal value due to ingestion of a diet or health foods and so forth rich in omega-3 unsaturated fatty acids. In addition, this balance modification is thought to be performed by significantly lowering the level of omega-6 unsaturated fatty acids that have risen above the normal value and inhibiting the significant decrease in the level of omega-3 unsaturated fatty acids below the normal value due to ingestion of a diet or health foods and so forth rich in omega-6 unsaturated fatty acids. The modifying action produced by the active ingredient of the present invention is demonstrated more effectively when the final products in the body, such as EPA and DHA or DGLA and AA, are ingested in excess.

Thus, the balance modifier or food composition of the present invention is more effective in persons consuming a diet rich in fish or meat, and persons consuming foods laden with omega-3 unsaturated fatty acids and/or omega-6 unsaturated fatty acids. When consumption of fish or meat tends to be regularly unbalanced, the balance modifier or food composition of the present invention can be taken or ingested before, after or during meals. In addition, in the case of health foods rich in omega-3 unsaturated fatty acids or omega-6 unsaturated fatty acids, the balance modifier of the present invention can be added to said health foods or the balance modifier or food composition of the present invention can be used in combination with said health foods.

For example, although soft capsules comprising oil containing EPA and DHA obtained by purification of fish oil are sold as EPA products, the active ingredient of the present invention can be contained to said EPA product or soft capsules containing the active ingredient of the present invention can be ingested with said EPA product to inhibit the detrimental effects on the body caused by excessive ingestion of EPA. In addition, although prepared powdered milk containing fish oil has been placed on the market in recent years for the purpose of adding DHA, the omega-6/omega-3 unsaturated fatty acid balance modifier of the present invention can be contained to said prepared powdered milk.

In the case of using the derivative of the present invention as a pharmaceutical, any type of formulation may be used provided oral administration or parenteral administration can be performed easily, examples of which include injections, infusions, powders, granules, tablets, capsules, enteric coated pills, troches, liquid for internal use, suspensions, emulsions, syrups, liquid for external use, fomentations, nasal drops, ear drops, eye drops, inhalants, ointments, lotions, suppositories and transintestinal nutrient preparations. These can be used either alone or in combination according to symptoms.

Each of these preparations can be formulated using known adjuvants that can be conventionally used in the field of pharmaceutical preparation technology, such as a vehicle, binder, antiseptic, stabilizer, disintegration agent, lubricator or corrective, with the primary drug according to the purpose of administration in accordance with routine methods. For example, in the case of preparing an injection, a solubilizer for pharmaceutical products such as a non-ionic surface activator can be used. More specifically, a preparation can be prepared by heating and dissolving the derivative of the present invention in 80 volumes of a non-ionic surfactant such as POE(60) cured castor oil or POE sorbitan monooleate followed by diluting with physiological saline. In addition, an isotonic agent, stabilizer, antiseptic or analgesic may be suitably added as necessary.

In addition, in the case of external preparations, ointments, creams and so forth can be prepared according to routine methods using vaseline, paraffin, fat and oils, lanolin, macrogol and so forth for the base. In addition, although the dose varies according to the purpose of administration and status of the patient (sex, age, body weight, etc.), the normal adult dose in the case of oral administration in terms of the total amount of derivative of the present invention is 1 mg to 10 g per day, preferably 1 mg to 2 g per day, and more preferably 1 mg to 200 mg per day, while in the case of parenteral administration, the dose is 0.1 mg to 1 g per day, preferably 0.1 mg to 200 mg per day, and more preferably 0.1 mg to 100 mg per day, all of which can be suitably adjusted.

In addition, since the omega-6/omega-3 unsaturated fatty acid balance modifying action of the derivative of the present invention is enhanced by administration with antioxidant, and particularly tocopherols, although varying according to the purpose of administration and status of the patient (sex, age, body weight, etc.), the normal adult dose of the derivative of the present invention in the case of oral administration in terms of the total amount of derivative of the present invention is 0.1 mg to 2 g per day, preferably 0.1 mg to 500 mg per day, and more preferably 0.1 mg to 100 mg per day, while in the case of parenteral administration, the dose is 0.01 mg to 200 mg per day, preferably 0.01 to 50 mg per day, and more preferably 0.01 to 20 mg per day. Moreover, the blending ratio of the derivative of the present invention and antioxidant is 0.001 to 1000 parts by weight, preferably 0.01 to 100 parts by weight, and more preferably 0.1 to 100 parts by weight of antioxidant per 1 part by weight of the derivative of the present invention, all of which can be suitably adjusted.

Since the derivatives of the present invention are compounds found in conventional foods or similar compounds, it is clear that they are superior in terms of safety. In addition, when sesamin was administered daily for 2 weeks (oral administration) at 2.14 g/day/kg to 7 week old, male IRC mice, there were no abnormalities observed, thereby confirming the above-mentioned safety.

Examples of food compositions containing the balance modifier of the present invention include general foods, functional foods, nutritional supplements, premature infant formula, infant formula, baby food, pregnancy foods and geriatric foods.

Although there are no particular restrictions on the food form, the food composition may be in the form of powdered or liquid premature infant or infant formula, ordinary solid or liquid foods, or foods containing oils. Examples of foods containing oils include natural foods containing oils such as meat, fish or nut, foods to which oils are added during preparation such as Chinese food, Chinese noodles and soups, foods prepared using oils as a heat medium such as tempura, fried fish, fried bean curd, fried rice, doughnuts and fried confections, oily foods or processed foods to which oils are added during processing such as butter, margarine, mayonnaise, salad dressing, chocolate, instant Chinese noodles, caramel, cookies and ice cream, and foods that are sprayed or coated with oils during final processing such as rice crackers, soda crackers and breads.

However, these examples are not limited to foods containing oils, but also include agricultural foods such as bread, noodles, rice, confections, bean curd and their processed foods, fermented foods such as rice wine and pharmaceutical alcoholic beverages, dairy products such as sweet rice wine, vinegar, soy sauce, fermented bean paste, salad dressing, yogurt, ham, bacon, sausage and mayonnaise, marine foods such as pressed fish, deep-fried shrimp and fish cake, and beverages such as fruit juice, soft drinks, sports drinks, alcoholic beverages and tea.

In addition, in the case of using the balance modifier of the present invention as a health food, functional food or nutritional supplement and so forth, the form used may be the form of the above-mentioned pharmaceuticals or foods and drinks, examples of which include a mixture of the active ingredient of the present invention with vegetable oil, fish oil or microbial oil (e.g. microbial oil containing EPA and/or DHA, microbial oil containing GLA or microbial oil containing DGLA and/or AA) that is encapsulated, powdered or granulated, a processed foods such as natural liquid foods; semi-digested nutritional foods; component nutritional foods containing proteins (although proteins such as milk protein, soy bean protein and egg albumin having balanced amino acids and high nutritional value are commonly used for the protein source, their degradation products, egg white oligopeptides, soy bean hydrolysates as well as mixtures of individual amino acids are also used), sugars, fats, trace elements, vitamins, emulsions and perfumes; drinks or transintestinal nutrient preparations.

In addition, while the food composition of the present invention can be used in healthy persons, it can also be used, for example, in the form of meals to which the balance modifier of the present invention has been added under the supervision of a nutritionist based on the instructions of a physician.

The food composition of the present invention can be processed and manufactured according to routine manufacturing methods using the balance modifier of the present invention and the food raw material (and particularly a raw material that does not substantially contain the active ingredient of the present invention). Although varying according to the properties of the drug form or food form, the content of the balance modifier of the present invention is typically at least 0.001%, preferably at least 1.4%, and more preferably at least 2%, although there are no particular limitations.

In the present invention, although examples of food raw materials not substantially containing the active ingredient of the present invention include food raw materials other than, for example, sesame, even if sesame is used as the food raw material, foods in which the amount of effective ingredient of the present invention contained in the finished product is extremely low and the total content of the active ingredient of the present invention is less than 0.1 mg, and preferably 0.8 mg or less, per amount of that product ingested per day, and foods in which the total content of sesamin, sesaminol, episesamin, episesaminol, sesamolin, 2-(3,4-methylenedioxyphenyl)-6-(3-methoxy-4-hydroxyphenyl)-3,7-dioxabicyclo(3.3.0)octane, 2,6-bis-(3-methoxy-4-hydroxyphenyl)-3,7-dioxabicyclo(3.3.0) octane, and 2-(3,4-methylenedioxyphenyl)-6-(3-methoxy-4-hydroxyphenoxy)-3,7-dioxabicyclo(3.3.0)octane is less than 0.1 mg, and preferably 0.8 mg or less, per amount of that product ingested per day are included in food raw materials that do not substantially contain the derivative of the present invention.

It is desirable to orally ingest the food composition of the present invention in an amount of 1 mg to 10 g, preferably 1 mg to 2 g and more preferably 1 mg to 200 mg per day in terms of the total amount of the derivative of the present invention for the purpose of adjusting the balance of omega-6 and omega-3 unsaturated fatty acids to the normal value after it has broken down due to an unbalanced diet.

Moreover, in the food composition of the present invention, in the case the balance modifier of the present invention has for its active ingredient the derivative of the present invention and an antioxidant, it is preferable that said food composition be orally ingested in an amount of 0.1 mg to 2 g, preferably 0.1 mg to 500 mg and more preferably 0.1 mg to 100 mg per day in terms of the total amount of the derivative of the present invention, and that the blending ratio of the derivative of the present invention and antioxidant be 0.001 to 1000 parts by weight, preferably 0.01 to 100 parts by weight and more preferably 0.1 to 100 parts by weight of antioxidant per 1 part by weight of the derivative of the present invention, since balance modifying effects are enhanced by an antioxidant.

Furthermore, in the case of adding the derivative of the present invention to a food raw material that does not substantially contain the derivative of the present invention but contains an antioxidant, and particularly tocopherols, the derivative of the present invention can be added so that the content ratio of the derivative of the present invention and antioxidant in the finished product is 0.001 to 1000 parts by weight, preferably 0.01 to 100 parts by weight and more preferably 0.1 to 100 parts by weight of antioxidant per 1 part by weight of the derivative of the present invention. At this time, antioxidant can be further added as necessary.

Next, a specific explanation is provided of the present invention through Examples.

EXAMPLES

Example 1

Three week old, male Wistar rats (Saitama Laboratory Animal Co., Ltd.) were preliminarily kept for 1 week on solid feed (CE-2, Japan Clea Co., Ltd.). The animals were divided into six groups of 6 animals each. The animals were then raised on standard feed (prepared by Eizai Co., Ltd.) composed of 20% casein, 15% cornstarch, 25% sucrose, 25% glucose, 0.3% DL-methionine, 5% cellulose, 0.2% choline bitartrate, 3.5% mineral mixture, 1% vitamin mixture and 5% prepared lipids. The sesamin adding groups were given feed in which 0.5% by weight of a purified mixture of sesamin and episesamin (sesamin: 51.3%, episesamin: 47.8%) was added to the standard feed. The following indicates the prepared lipids used for each group along with the addition or non-addition of sesamin.

Group 1: Linoleic acid group
  Rapeseed oil:Soybean oil=7:3
  (omega-6:omega-3=3:1)
Group 2: Linoleic acid+sesamin group
  Rapeseed oil:Soybean oil 7:3
  (omega-6:omega-3=3:1)
Group 3: α-Linolenic acid group
  Beefsteak plant oil:Safflower oil=7:3
  (omega-6:omega-3=1:3)
Group 4: α-Linolenic acid+sesamin group
  Beefsteak plant oil:Safflower oil=7:3
  (omega-6:omega-3=1:3)
Group 5: Eicosapentaenoic acid (EPA) group
  Rapeseed oil:EPA=3:2
Group 6: Eicosapentaenoic acid (EPA)+sesamin group
  Rapeseed oil:EPA=3:2

Note that in the EPA group, 5,8,11,14,17-eicosapentaenoic acid ethyl ester (97%) was used for the EPA, and it was prepared so that it was substituted with an amount of EPA nearly equal to the amount of α-linolenic acid of the α-linolenic acid group. The fatty acid compositions of the prepared lipids used in each of the groups described above are shown in Table 1. The animals were fed for 27 days using the feed assigned to each group and then sacrificed after 1 day of fasting followed by removal of the liver, serum, kidneys, lungs, heart and brain. After extracting the lipids using the method of Folch, fatty acid methyl esters were prepared in accordance with routine methods, and the fatty acid compositions were quantified with gas chromatography. The fatty acid compositions in the liver of each experimental. group are shown in Table 2, while the ratios of omega-6 and omega-3 unsaturated fatty acids in the liver of each. experimental group are shown in Table 3.

TABLE 1

| Fatty Acid Compositions of Prepared Lipids (%) | | | | | | |
|---|---|---|---|---|---|---|
| | 16:0 | 18:0 | 18:1 (n-9) | 18:2 (n-6) | 18:3 (n-3) | 20:5 (n-3) |
| Linoleic acid group (n-6:n-3 3:1) Rapeseed oil:Soybean oil = 7:3 | 5.9 | 2.3 | 48.5 | 31.2 | 9.9 | |
| α-linolenic acid group (n-6:n-3 = 1:3) Beefsteak plant oil:safflower oil = 7:3 | 6.7 | 2.1 | 36.7 | 14.1 | 40.3 | |
| EPA group Rapeseed oil:EPA = 3:2 | 2.4 | 1.0 | 35.2 | 13.1 | 6.5 | 40.0 |

16:0: Palinitic acid
18:0: Stearic acid
18:1 (n-9): Oleic acid
18:2 (n-6): Linoleic acid
18:3 (n-3): α-Linolenic acid

TABLE 1-continued

Fatty Acid Compositions of Prepared Lipids (%)

| | 16:0 | 18:0 | 18:1 (n-9) | 18:2 (n-6) | 18:3 (n-3) | 20:5 (n-3) |
|---|---|---|---|---|---|---|

20:5 (n-3): 5,8,11,14, 17-eicosapentaenoic acid
EPA: 5,8,11,14,17-eicosapentaenoic acid ethyl ester (97%)
(n-3): omega-3 unsaturated fatty acid
(n-6): omega-6 unsaturated fatty acid
(n-9): omega-9 unsaturated fatty acid

TABLE 2

Effects of Sesamin and Ingested Fatty Acids on Fatty Acid Composition in the Liver ($\mu$mol/g)

| | Linoleic acid | | $\alpha$-Linolenic acid | | EPA | |
|---|---|---|---|---|---|---|
| Sesamin | − | + | − | + | − | + |
| 16:0 | 21.7 ± 3.42 | 25.2 ± 4.53 | 22.5 ± 2.45 | 29.0 ± 2.03 | 31.4 ± 5.03 | 32.3 ± 4.09 |
| 18:0 | 17.6 ± 2.67 | 18.9 ± 2.65 | 18.2 ± 2.01 | 22.3 ± 1.57 | 23.4 ± 2.99 | 24.3 ± 2.71 |
| 18:1 (n-9) | 19.1 ± 4.13 | 17.4 ± 5.83 | 15.1 ± 2.31 | 15.8 ± 2.02 | 23.4 ± 5.22 | 20.3 ± 3.26 |
| 18:2 (n-6) | 10.7 ± 2.04 | 8.36 ± 1.60 | 14.8 ± 3.50 | 13.8 ± 0.99 | 11.1 ± 1.57 | 11.4 ± 1.02 |
| 18:3 (n-3) | 0.83 ± 0.21 | 0.22 ± 0.23*** | 6.53 ± 2.16 | 2.25 ± 0.34*** | 1.30 ± 0.54 | 0.32 ± 0.08*** |
| 20:3 (n-6) | 0.55 ± 0.11 | 1.09 ± 0.20*** | 0.77 ± 0.06 | 1.60 ± 0.19*** | 0.73 ± 0.12 | 1.70 ± 0.22*** |
| 20:4 (n-6) | 21.1 ± 3.39 | 24.7 ± 2.51 | 16.1 ± 2.25 | 25.6 ± 2.05*** | 9.18 ± 0.76 | 13.6 ± 1.54*** |
| 20:5 (n-3) | 0.31 ± 0.26 | 0.03 ± 0.06* | 2.40 ± 0.49 | 0.88 ± 0.08*** | 25.4 ± 9.15 | 11.5 ± 2.12*** |
| 22:5 (n-3) | 0.78 ± 0.17 | 0.78 ± 0.33 | 1.73 ± 0.25 | 2.02 ± 0.17 | 8.10 ± 1.60 | 5.96 ± 1.38 |
| 22:6 (n-3) | 6.19 ± 1.53 | 7.14 ± 0.76 | 6.94 ± 0.93 | 9.15 ± 0.48 | 9.29 ± 1.95 | 7.54 ± 0.88 |
| Totals | 98.9 ± 16.0 | 103.7 ± 18.0 | 105.1 ± 14.6 | 122.6 ± 8.57* | 143.4 ± 25.6 | 129.0 ± 15.2 |

Significant difference according to presence or absence of administrated sesamin among dose groups ingesting the same fatty acid:
*$p < 0.025$,
***$p < 0.005$
16:0 = palmitic acid, 18:0 = stearic acid, 18:1(n-9) = oleic acid, 18:2(n-6) = linoleic acid, 18:3(n-3) = $\alpha$-linolenic acid, 20:3(n-6) = dihomo-$\gamma$-linolenic acid, 20:4(n-6) = arachidonic acid, 20:5(n-3) = eicosapentaenoic acid, 22:5 (n-3) = docosapentaenoic acid, 22:6(n-3) = docosahexaenoic acid
(n-3): omega-3 unsaturated fatty acid
(n-6): omega-6 unsaturated fatty acid
(n-9): omega-9 unsaturated fatty acid

TABLE 3

Effects of EPA and Sesamin Administration on omega-6/omega-3 Balance in the Liver ($\mu$mol/g)

| | Sesamin | omega-6 unsaturated fatty acids | omega-3 unsaturated fatty acids | omega-6/omega-3 |
|---|---|---|---|---|
| Linoleic acid | − | 32.4 ± 5.41 | 8.10 ± 1.74 | 3.76 ± 0.27 |
| | + | 34.1 ± 4.18 | 8.15 ± 1.15 | 4.20 ± 0.20** |
| $\alpha$-linolenic acid | − | 31.7 ± 5.65 | 17.6 ± 3.23 | 1.81 ± 0.16 |
| | + | 41.2 ± 2.90*** | 14.3 ± 0.88 | 2.87 ± 0.13*** |
| EPA | − | 21.1 ± 2.19 | 44.1 ± 12.5 | 0.50 ± 0.08 |
| | + | 26.7 ± 2.47*** | 25.3 ± 4.13*** | 1.07 ± 0.11*** |

Significant difference between group to which sesamin was added to feed and group in which it was not added to feed among groups given the same dietary fatty acids: *$p < 0.025$, $p < 0.01$, *$p < 0.005$ In the omega-3 unsaturated fatty acid addition group i.e., the $\alpha$-linolenic acid and EPA group, arachidonic acid content in the liver decreased and a particularly remarkable decrease was observed in the EPA addition group. The decrease was significantly improved by administration of sesamin. Next, the ratios of omega-3 unsaturated fatty acids and omega-6 unsaturated fatty acids in the liver, lung, heart, kidney and brain are shown in FIG. 1. In the linoleic acid group, the ratio of omega-6 and omega-3 unsaturated fatty acids is 3:1 which is desirable for ingested lipids, and the ratio of omega-3 and omega-6 unsaturated fatty acids of each tissue in this group was considered to be at the normal level.

This normal balance was not observed to be affected by administration of sesamin in any of the tissues. On the other hand, in the $\alpha$-linolenic acid and EPA group, which is an omega-3 unsaturated fatty acid ingestion group, the ratio of omega-6 unsaturated fatty acids decreased in each tissue, and the decreases were observed to be more remarkable in the EPA group in which there is a higher degree of unsaturation. However, sesamin administration caused the ratio of omega-6 unsaturated fatty acids to rise and improve.

The degree of sesamin-induced improvement was demonstrated more prominently in the EPA group in which was observed a remarkable decrease in the ratio of omega-6 unsaturated fatty acids. Based on the above findings, sesamin was clearly shown to modify the balance of fatty acids to a suitable ratio of omega-6 unsaturated fatty acids and omega-3 unsaturated fatty acids in each tissue of the body in order to maintain homeostasis and prevent disease.

Example 2

Three week old, male Wistar rats (Saitama Laboratory Animal Co., Ltd.) were preliminarily kept for 1 week on solid feed (CE-2, Japan Clea Co., Ltd.). The animals were divided into seven groups of 6 animals each. The animals were then raised on the standard feed used in Example 1. The same prepared lipids used for the linoleic acid group in Example 1 in which rapeseed oil:soybean oil=7:3 were used for Group 1. The same prepared lipids as the EPA group in Example 1 were used for the remaining six groups (rapeseed oil:EPA=3:2). For the dioxabicyclo(3.3.0)octane derivatives, sesaminol (Compound A) purified from refined sesame oil, sesamolin (Compound B), prepared from crude sesame oil, 2-(3,4-methylenedioxyphenyl)-6-(3-methoxy-4-hydroxyphenyl)-3,7-dioxabicyclo(3.3.0)octane (Compound C), 2,6-bis-(3-methoxy-4-hydroxyphenyl)-3,7-dioxabicyclo (3.3.0)octane (Compound D) and 2-(3,4-methylenedioxyphenyl)-6-(3-methoxy-4-hydroxyphenoxy)-3,7-dioxabicyclo(3.3.0)octane (Compound E) prepared from an extract of sesame seeds were used by adding 0.5% by weight after preparing in accordance with a previously filed patent (Japanese Patent Application No. 63-53642). The following indicates the prepared lipids used for each group along with the dioxabicyclo(3.3.0)octane derivative that was added.

Group 1: Linoleic acid group
    Rapeseed oil:Soybean oil=7:3
    (omega-6:omega-3=3:1)
Group 2: EPA group
    Rapeseed oil:EPA=3:2
Group 3: EPA+Compound A Group
    Rapeseed oil:EPA=3:2
Group 4: EPA+Compound B Group
    Rapeseed oil:EPA=3:2
Group 5: EPA+Compound C Group
    Rapeseed oil:EPA=3:2
Group 6: EPA+Compound D Group
    Rapeseed oil:EPA=3:2

Group 7: EPA+Compound E Group
    Rapeseed oil:EPA=3:2

The animals were fed for 27 days using the feed assigned to each group and then sacrificed after 1 day of fasting followed by removal of the liver. After extracting the lipids using the method of Folch, fatty acid methyl esters were prepared in accordance with routine methods, and the fatty acid compositions were quantified with gas chromatography. The arachidonic acid contents in the liver of Groups 1 through 7 were 21.1±3.39, 9.18±0.76, 12.8±1.10, 11.8±0.98, 10.9±1.07, 12.1±1.20 and 11.5±0.49 ($\mu$mol/g), respectively.

Although a remarkable decrease in arachidonic acid content in the liver was observed due to ingestion of EPA, this was significantly improved by administration of dioxabicyclo(3.3.0)octane derivative. As has been described above, dioxabicyclo(3.3.0)octane derivative was clearly shown to modify the balance of fatty acids to a suitable ratio of omega-6 unsaturated fatty acids and omega-3 unsaturated fatty acids in each tissue of the body in order to maintain homeostasis and prevent disease.

Example 3

Rats were fed using the same materials and procedure as Example 1 with the exception of the prepared lipids. The following indicates the prepared lipids used for each group along with the addition or non-addition of sesamin.

Group 1: Linoleic acid group
    Soybean oil:Beefsteak plant oil=5:1
    (omega-6:omega-3=2.7:1)
Group 2: Linoleic acid+sesamin group
    Soybean oil:Beefsteak plant oil=5:1
    (omega-6:omega-3=2.7:1)
Group 3: Arachidonic acid group
    Beefsteak plant oil:Palm oil:AA=2:1:2
    (omega-6:omega-3=3.6:1)
Group 4: Arachidonic acid+sesamin group
    Beefsteak plant oil:Palm oil:AA=2:1:2
    (omega-6:omega-3=3.6:1)

Note that in arachidonic acid groups, arachidonic ethyl ester (99%) was used for the AA, the total amount of omega-6 unsaturated fatty acids was made to be equal to that of the arachidonic acid group and linoleic acid group, and the arachidonic acid group was prepared so that the majority of linoleic acid in the linoleic acid groups was substituted with arachidonic acid. The fatty acid compositions of the prepared lipids used in each of the groups described above are shown in Table 4.

TABLE 4

Fatty Acid Compositions of Prepared Lipids (%)

| | 16:0 | 18:0 | 18:1 (n-9) | 18:2 (n-6) | 18:3 (n-3) | 20:4 (n-6) |
|---|---|---|---|---|---|---|
| Linoleic acid group (n-6:n-3 = 2.7:1) Soybean oil:Beefsteak plant oil = 5:1 | 9.53 | 3.44 | 22.55 | 46.25 | 17.21 | 0 |
| Arachidonic acid group (n-6:n-3 = 3.6:1) Beefsteak plant oil:palm oil:AA = 2:1:2 | 18.82 | 2.12 | 18.54 | 6.66 | 12.88 | 40.0 |

AA: Arachidonic acid ethyl ester (99%)

The animals were fed for 27 days using the feed assigned to each group and then sacrificed after 1 day of fasting followed by removal of the liver, serum, kidneys, lungs, heart and brain. After extracting the lipids using the method of Folch, fatty acid methyl esters were prepared in accordance with routine methods, and the fatty acid compositions were quantified with gas chromatography. The fatty acid compositions in the liver of each experimental group are shown in Table 5, while the ratios of omega-6 and omega-3 unsaturated fatty acids in the liver of each experimental group are shown in Table 6.

TABLE 5

Effects of Sesamin and Ingested Fatty Acids on Fatty Acid Composition in the Liver ($\mu$mol/g tissue)

| | Linoleic acid | | Arachidonic acid | |
|---|---|---|---|---|
| Sesamin | − | + | − | + |
| 18:0 | 25.9 ± 4.90 | 24.0 ± 2.09 | 23.6 ± 2.86 | 22.2 ± 0.73 |
| 18:1 (n-9) | 26.4 ± 6.78 | 17.0 ± 5.17 | 17.2 ± 4.32* | 13.1 ± 0.87*** |
| 18:2 (n-6) | 28.3 ± 7.27 | 15.9 ± 2.16** | 3.85 ± 0.64*** | 2.99 ± 0.24*** |
| 18:3 (n-6) | 0.53 ± 0.17 | 0.16 ± 0.04*** | 0.45 ± 0.11 | 0.10 ± 0.03***c |
| 18:3 (n-3) | 4.02 ± 1.29 | 0.92 ± 0.20*** | 2.82 ± 0.73 | 0.55 ± 0.08***c |
| 20:3 (n-6) | 0.69 ± 0.14 | 1.20 ± 0.27*** | 0.61 ± 0.17 | 0.42 ± 0.10*** |
| 20:4 (n-6) | 29.8 ± 5.05 | 32.5 ± 3.16 | 71.7 ± 14.0*** | 42.2 ± 1.64***c |
| 20:5 (n-3) | 0.84 ± 0.17 | 0.20 ± 0.05*** | 0.47 ± 0.19** | 0.03 ± 0.03***c |
| 22:5 (n-3) | 1.60 ± 0.19 | 1.45 ± 0.20 | 2.00 ± 0.50 | 1.83 ± 0.48 |
| 22:6 (n-3) | 9.13 ± 1.27 | 9.08 ± 1.14 | 5.50 ± 1.16*** | 5.68 ± 1.12*** |

Significant difference relative to linoleic acid group: *p < 0.025, p < 0.01, *p < 0.005
Significant difference between arachidonic acid group and arachidonic acid + sesamin group: c: p < 0.005

TABLE 6

Effects of AA and Sesamin Administration on omega-6/omega-3 Balance in the Liver ($\mu$mol/g tissue)

| | Sesamin | omega-6 unsaturated fatty acids | omega-3 unsaturated fatty acids | omega-6/omega-3 |
|---|---|---|---|---|
| Linoleic acid | − | 59.7 ± 12.0 | 15.8 ± 1.79 | 3.78 ± 0.61 |
| | + | 50.1 ± 5.24 | 11.8 ± 1.45*** | 4.27 ± 0.33 |
| Arachidonic acid | − | 82.0 ± 16.1* | 11.0 ± 2.18*** | 7.58 ± 1.09*** |
| | + | 47.6 ± 1.83f | 8.24 ± 1.52*c,d | 5.95 ± 1.24*b |

Significant difference relative to linoleic acid group: ***p < 0.005
Significant difference between linoleic acid + sesamin group and arachidonic acid + sesainin group: bp < 0.01, cp < 0.005
Significant difference between arachidonic acid group and arachidonic acid + sesamin group: dp < 0.025, fp < 0.005

The ingested amount of linoleic acid is preferably such that the ratio of omega-6 and omega-3 unsaturated fatty acids is 2.7:1 as ingested lipids. The ratio of omega-3 and omega-6 unsaturated fatty acids in each tissue of this group is considered to be at the normal level. On the other hand, in the arachidonic acid group, although it is desirable to ingest this fatty acid so that the ratio of omega-6 and omega-3 unsaturated fatty acids is 3.6:1 as ingested lipids, due to excessive ingestion of arachidonic acid, the content of arachidonic acid in the liver increased remarkably and an increase was also observed in the amount of omega-6 unsaturated fatty acids. This condition was significantly improved by administration of sesamin, however. Next, FIG. 2 indicates the ratios of omega-3 unsaturated fatty acids and omega-6 unsaturated fatty acids in the liver, lung, heart, kidney and brain.

Example 4

2.4 g of the mixture of the derivative of the present invention used in Example 1 was added to 100 g of butterfat from which the buttermilk had been removed in the churning procedure of the butter production process. This was followed by working to form a homogeneous composition and obtain butter having the action of modifying the balance of omega-6 and omega-3 unsaturated fatty acids.

Example 5

0.5 g of the derivative of the present invention was mixed with 20.5 g of silicic anhydride followed by the addition of 79 g of cornstarch and further mixing. 100 ml of a 10% hydroxypropylcellulose-ethanol solution were added to this compound followed by kneading, extrusion and drying in accordance with routine methods to obtain granules.

Example 6

7 g of the mixture of the derivative of the present invention used in Example 1 was mixed with 20 g of silicic anhydride followed by the addition of 10 g of microcrystalline cellulose, 3 g of magnesium stearate and 60 g of lactose and mixing. This mixture was then formed into tablets using a single-action tablet making machine to produce tablets having a diameter of 7 mm and weighing 100 mg.

Example 7

2.5 g of the derivative of the present invention was heated and dissolved in 200 g of TO-10M (Nikko Chemicals), a non-ionic surface activator, followed by the addition of 4.7975 liters of sterile physiological saline heated to 60° C. After stirring well, the solution was antiseptically filled into vials and sealed to produce injection preparations.

Example 8

Water was added to 100 parts by weight of gelatin and 35 parts by weight of food-additive glycerin, and the mixture was melted at 50–60° C. to prepare a gelatin coating having a viscosity of 20,000 cps. Next, 95.1% wheat germ oil, 2.9% vitamin E oil and 2% of the mixture of the derivative of the present invention used in Example 1 were mixed to prepare the contents for the above-mentioned gelatin coating. Using the coating and its contents, capsules were formed and dried in accordance with routine methods to produce soft capsules containing 180 mg of the above-mentioned contents per capsule. Each said capsule contained 3.6 mg of the mixture of the derivative of the present invention and 2.34 mg of α-tocopherol.

Example 9

1 g of tuna oil (arachidonic acid=2.1%, eicosapentaenoic acid=3.6%, docosahexaenoic acid=15.6%) and 100 mg of the mixture of the derivative of the present invention used in Example 1 were blended with 100 g of powdered milk raw material to produce powdered milk in accordance with routine methods. As a result, a prepared powdered milk was obtained that contained omega-6/omega-3 unsaturated fatty acid balance modifier.

INDUSTRIAL APPLICABILITY

The omega-3/omega-6 unsaturated fatty acid balance modifier of the present invention is effective in maintaining homeostasis in the body and preventing disease since it is able to easily regulate the balance of omega-3 unsaturated fatty acids and omega-6 unsaturated fatty acids to an ideal value without placing any particular restrictions on dietary content. In addition, it is also superior in terms of its safety and can be used in various foods.

I claim:

1. A method for modifying the balance of omega-6 and omega-3 unsaturated fatty acids comprising administrating a dioxabicyclo(3.3.0)octane derivative having a formula (I):

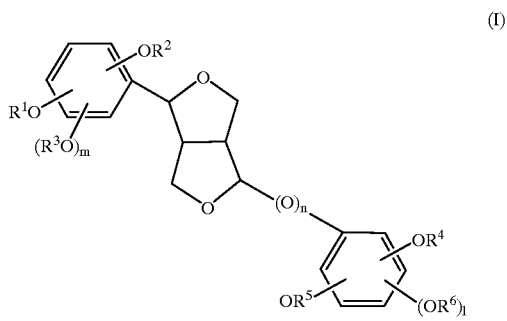

wherein, $R^1$, $R^2$, $R^3$, $R^4$, $R^5$ and $R^6$ are respectively and independently a hydrogen atom or alkyl group having 1–3 carbon atoms, or $R^1$ and $R^2$ and/or $R^4$ and $R^5$ together represent a methylene group or ethylene group, and n, m and l represent 0 or 1.

2. A method as set forth in claim 1 wherein said dioxabicyclo(3.3.0)octane derivative is at least one of the compounds selected from sesamin, sesaminol, episesamin, episesaminol, sesamolin, 2-(3,4-methylenedioxyphenyl)-6-(3-methoxy-4-hydroxyphenyl)-3,7-dioxabicyclo( 3.3.0) octane, 2,6-bis-(3-methoxy-4-hydroxyphenyl)-3,7-dioxabicyclo(3.3.0) octane, and 2-(3,4-methylenedioxyphenyl)-6-(3-methoxy-4-hydroxyphenoxy)-3,7-dioxabicyclo(3.3.0)octane.

3. A method as set forth in claim 1 wherein said omega-3 unsaturated fatty acid is at least one of 9,12,15-octadecatrienoic acid (α-linolenic acid), 6,9,12,15-octadecatetraenoic acid, 8,11,14,17-eicosatetraenoic acid, 5,8,11,14,17-eicosapentaenoic acid, 7,10,13,16,19-docosapentaenoic acid and 4,7,10,13,16,19-docosahexaenoic acid.

4. A method as set forth in claim 1 wherein said omega-6 unsaturated fatty acid is at least one of 9,12-octadecadienoic acid (linoleic acid), 6,9,12-octadecatrienoic acid (γ-linolenic acid), 8,11,14-eicosatrienoic acid (dihomo-γ-linolenic acid) and 5,8,11,14-eicosatetraenoic acid (arachidonic acid).

5. A method as set forth in claim 1 comprising administering an antioxidant together with said dioxabicyclo(3.3.0) octane derivative.

6. A method as set forth in claim 5 wherein said antioxidant is a tocopherol.

* * * * *